US006225093B1

(12) United States Patent
Grant et al.

(10) Patent No.: US 6,225,093 B1
(45) Date of Patent: May 1, 2001

(54) DETECTION OF C4A DELETION BY LONG RANGE PCR

(75) Inventors: Struan Grant, Reykjavik; Thorarinn Blöndal, Gardabaer, both of (IS)

(73) Assignee: deCODE genetics ehf. (IS)

( * ) Notice: Subject to any disclaimer, the term of this patent is extended or adjusted under 35 U.S.C. 154(b) by 0 days.

(21) Appl. No.: 09/470,673

(22) Filed: Dec. 23, 1999

Related U.S. Application Data

(63) Continuation-in-part of application No. 09/391,244, filed on Sep. 7, 1999, now abandoned.

(51) Int. Cl.[7] .............................. C07H 21/04; C12Q 1/68; C12P 19/34
(52) U.S. Cl. ...................... 435/91.2; 536/23.4; 536/24.31
(58) Field of Search .................... 435/91.2, 6; 536/23.4, 536/24.31

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,965,188 | 10/1990 | Mullis et al. | 435/6 |
| 5,512,462 | 4/1996 | Cheng | 435/91.2 |

OTHER PUBLICATIONS

Andersson, G. et al., "Retroelements in the Human MHC Class II Region," *Trends Genet.*, 14(3):109–114 (1998).

Arnett, F.C. and Moulds, J.M., "HLA Class III Molecules and Autoimmune Rheumatic Diseases," *Clin. Exp. Rheumatol.*, 9(3):289–296 (1991).

Babon, J.J., et al., "Improved Strategy for Mutation Detection—A Modification to the Enzyme Mismatch Cleavage Method," *Nucl. Acids Res.*, 23(4):5082–5084 (1995).

Barba, G.M.R., et al., "A New PCR–based Typing of the Rodgers and Chido Antigenic Determinants of the Fourth Component of Human Complement," *Eur. J. Immunogenetics*, 21(5):325–339 (1994).

Belt, K.T., et al., "The Structural Basis of the Multiple Forms of Human Complement Component C4," *Cell*, 36(4):907–914 (1984).

Burland, V. and Kusukawa, N., "Long PCR Facilitates Concise Cloning and Sequencing with a Minimal Tiling Set of Templates," *Biotechniques*, 23(6):1070–1075 (1997).

(List continued on next page.)

*Primary Examiner*—Jeffrey Fredman
*Assistant Examiner*—Juliet C Einsmann
(74) *Attorney, Agent, or Firm*—Hamilton, Brook, Smith & Reynolds, P.C.

(57) ABSTRACT

Methods are described for detecting a deletion in the C4A gene (e.g., for detecting C4AQ0), by performing long range polymerase chain reaction amplification on a test sample comprising genomic DNA. The methods amplify target DNA comprising a retroviral insert in intron 9 of the C4A gene using primers designed such that PCR products are formed only if the test sample comprises genomic DNA comprising a deletion in the C4A gene; alternatively, the methods amplify target DNA comprising the junction between intron 9 and the retroviral insert in intron 9 of the C4A gene using primers designed such that PCR products are formed only if the test sample comprises genomic DNA that does not comprise the deletion in the C4A gene. Alternatively, primers are designed such that PCR products have detectably different sizes, depending on whether or the test sample comprises genomic DNA that comprises the deletion in the C4A gene. The methods can be used to identify whether an individual is at risk for systemic lupus erythematosus, as the presence of a deletion in the C4A gene correlates with risk for the disease, and can also be used for C4A deletion genotyping of an individual.

14 Claims, 1 Drawing Sheet

OTHER PUBLICATIONS

Cheng, S., et al., "Effective Amplification of Long Targets from Cloned Inserts and Human Genomic DNA," *Proc. Natl. Acad. Sci. USA,* 91(12):5695–5699 (1994).

Chu, X., et al., "Length Polymorphism of the Human Complement Component C4 Gene is Due to an Ancient Retroviral Integration," *Exp. Clin. Immunogenet.,* 12:74–81 (1995).

Christiansen, F.T., et al., "Complement Allotyping in SLE: Association with C4A Null," *Aust. NZ J. Med.,* 13(5):483–488 (1983).

Curran, M.D., et al., "Long–range PCR Amplification as an Alternative Strategy for Characterizing Novel HLA–B Alleles," *European J. Immonogenet.,* 23(4):287–309 (1996).

Dangel, A.W., et al., "The Dichotomous Size Variation of Human Complement C4 Genes is Mediated by a Novel Family of Endogenous Retroviruses, Which Also Establishes Species–specific Genomic Patterns Among Old World Primates," *Immongenetics 40(6)*:425–436 (1994).

Fielder, A.H., et al., Family Study of the Major Histocompatibility Complex in Patients with Systemic Lupus Erythematosus: Importance of Null Alleles of C4A and C4B in Determining Disease Susceptibility, *Bre. Med. J. (Clin. Res. Ed.),* 286(6362):425–428 (1983).

Fromenty, B., et al., "Efficient and Specific Amplification of Identified Partial Duplications of Human Mitochondrial DNA by Long PCR," *Biochem. Biophys. Acta,* 1308(3):222–230 (1996).

Gordadze, A.V. and Benes, H., "Long PCR–based Technique for Detection of Transposon Insertions In and Around Cloned Genes of *Drosophila melanogaster,*" *Biotechniques,* 21(6):1062–1066 (1996).

Hasuike, S., et al., "Isolation and Localization of an IDDMK1, 2–22–Related Human Endogenous Retroviral Gene, and Identification of a CA Repeat Marker at its Locus," *J. Hum. Genet.,* 44(4):343–347 (1999).

Hecimovic, S., "Expand Long PCR for Fragile X Mutation Detection," *Clin. Genet.,* 52(3):147–154 (1997).

Truedsson, L., et al., "Sharing of MHC Haplotypes Among Patients with Systemic Lupus Erythematosus from Unrelated Caucasian Multicase Families: Disease Association with the Extended Haplotype [HLA–B8, SC01, DR17]," *J. Rheumatology,* 22(10):1852–1861 (1995).

Holmes, Z.R., et al., "Characterization of a Large Chromosomal Deletion in the PROS1 Gene of a Patient with Protein S Deficiency Type I Using Long PCR," *Br. J. Haematol.,* 92(4):986–991 (1996).

Howard, P.F., et al., "Relationship Between C4 Null Genes, HLA–D Region Antigens, and Genetic Susceptibility to Systemic Lupus Erythematosus in Caucasian and Black Americans," *Am. J. Med.,* 81(2):187–193 (1986).

Kazazian, H.H. and Moran, J.V., "The Impact of L1 Retrotransposons on the Human Genome," *Nature Genetics,* 19:19–24 (1998).

Kemp, M.E., et al., "Deletion of C4A Genes in Patients with Systemic Lupus Erythematosus," *Arthritis Rheum.,* 30(9):1015–1022 (1987).

Kulski, J.K., et al., "Comparison Between Two Human Endogenous Retrovirus (HERV)–rich Regions Within the Major Histocompatibility Complex," *J. Mol. Evol.,* 48(6):675–683 (1999).

Kulski, J.K., et al., "Coevolution of PERB11 (MIC) and HLA Class I Genes with HERV–16 and Retroelements by Extended Genomic Duplication," *J. Mol. Evol.,* 49(1):84–97 (1999).

Kumar, A., et al., "DR3 and NonDR3 Associated Complement Component C4A Deficiency in Systemic Lupus Erythematosus," *Clin. Immunol. Immunopathol.,* 60(1):55–64 (1991).

Lower, R. et al., "The Viruses in All of Us: Characteristics and Biological Significance of Human Endogenous Retrovirus Sequences," *Proc. Natl. Acad. Sci. USA,* 93(11):5177–5184 (1996).

Mager, D.L., et al., "Endogenous Retroviruses Provide the Primary Polyadenylation Signal for Two New Human Genes (HHLA2 and HHLA3)," *Genomics,* 59(3):255–263 (1999).

Ratnoff, W.D., "Inherited Deficiencies of Complement in Rheumatic Diseases," *Rheumatic Dis. Clin. N. Am.,* 22(1):75–94 (1996).

Reveille, J.D., et al., "Null Alleles of the Fourth Component of Complement and HLA Haplotypes in Familial Systemic Lupus Erythematosus," *Immunogenetics,* 21(4):299–311 (1985).

Schneider, P.M., et al., "Polymorphism of the Human Complement C4 and Steroid 21–Hydroxylase Genes," *J. Clin. Invest.,* 78(3):650–657 (1986).

Schott, B., et al., "Efficient Recovery and Regeneration of Integrated Retroviruses," *Nucl. Acids Res.,* 25(14):2940–2942 (1997).

Shai, R., et al., "Genome–wide Screen for Systemic Lupus Erythematosus Susceptibility Genes in Multiplex Families," *Hum. Mol. Genet.,* 8(4):639–644 (1999).

Steen, V.M., et al., "Detection of the Poor Metabolizer–associated CYP2D6(D) Gene Deletion Allele by Long–PCR Technology," *Pharmacogenetics,* 5(4):215–223 (1995).

Steinsson, K., et al., "A Study of the Major Histocompatibility Complex in a Caucasian Family with Multiple Cases of Systemic Lupus Erythematosus: Association with the C4AQ0 Phenotype" *J. Rheumatology,* 22(10):1862–1866 (1995).

Steinsson, K., et al., "A Study of the Association of HLA DR, DQ, and Complement C4 Alleles with Systemic Lupus Erythematosus in Iceland," *Ann. Rheum. Dis.,* 57(8):503–505 (1998).

Taruscio, D. and Mantovani, A., "Eleven Chromosomal Integration Sites of a Human Endogenous Retrovirus (HERV 4–1) Map Close to Known Loci of Thirteen Hereditary Malformation Syndromes," *Teratology,* 54(2):108–110 (1996).

Van de Water, N., et al., "A 20.7kb Deletion Within the Factor VIII Gene Associated with LINE–1 Element Insertion," *Throm. Haemost.,* 79(5):938–942 (1998).

Van Houten, B., et al., "Development of Long PCR Techniques to Analyze Deletion Mutations of the Human hprt Gene," *Mutat. Res.,* 403:171–175 (1998).

Watnick, T.J., "An Unusual Pattern of Mutation in the Duplicated Portion of PKD1 is Revealed by Use of a Novel Strategy for Mutation Detection," *Hum. Mol. Genet.,* 6(9):1473–1481 (1997).

Kemp et al. Arthritis and Rheumatism, vol. 30, No. 9 (Sep. 1987) p. 1015–1022.*

Fredrikson et al. Human Immunology 59, 713–719 (1998) p. 713–719.*
Keinanen et al. Clinical Chemistry vol. 26, No. 6, p. 900–903.*
Chu et al. Experimental Clinical Immunogenet. 1995; 12:74–81.*
Cheng et al. PNAS USA 91:5695–5699, Jun. 1994.*

Steen et al. Pharmacogenetics (1995) 5, 215–223.*
Van Houten et al. Mutation Research 403(1998) 171–175.*
Sargent et al. Abstract Only. Human Molecular Genetics. 1994 3(3): 481–488.*

* cited by examiner

DETECTION OF C4A DELETION BY LONG RANGE PCR

RELATED APPLICATION(S)

This application is a Continuation-in-Part of U.S. Ser. No.: 09/391,244, filed on Sep. 7, 1999, now abandoned the entire teachings of which are incorporated herein by reference.

BACKGROUND OF THE INVENTION

Systemic lupus erythematosus (SLE) is an autoimmune disease characterized by immune dysregulation resulting in the production of anti-nuclear antibodies, the generation circulating immune complexes, and the activation of the complement system. SLE leads to inflammation of various parts of the body, especially the skin, joints, blood, kidneys, lungs heart and nervous system. SLE affects approximately 1 in every 500 Americans, and strikes women 10–15 times more frequently than men. It is more common among Asians, and in China, SLE may be even more common than rheumatoid arthritis.

Although there is evidence of genetic etiology, linkage analysis suggests that there are no 'major' susceptibility genes segregating in families with SLE (Shai, R., et al., *Hum. Mol. Genet.* 8:639–644 (1999)). Nevertheless, a number of studies have demonstrated an association between SLE and certain major histocompatibility complex (MHC) antigens (Fielder, A. H. et al., *Br. Med J. (Clin. Res. Ed.)*286(6363):425–8 (1983); Christiansen, F. T. et al., *Aust. NZ J. Med.* 13(5):483–8 (1983); Reveille, J. D. et al., *Immunogenetics* 21(4):299–311 (1985); Howard, P. F. et al., *Am. J. Med.* 81(2):187–193 (1986); Kemp, M. E. et al., *Arthritis Rheum.* 30(9):1015–1022 (1987)). Within the MHC region, found on the short arm of chromosome 6, are the genes for the fourth component of the complement system: C4A and C4B. These genes are highly homologous, with only an 8 nucleotide difference in exon 26. This difference leads to six amino acid changes which allow resolution on sodium dodecyl sulfate-polyacrylamide gel electrophoresis (SDS-PAGE) (Belt, K. T., et al., *Cell* 36(4):907–914 (1984)).

HLA-DR3 and a C4A null allele are frequently co-inherited as the extended haplotype B8,BfS:C2C, C4AQ0,C4B1;DR3. This is the most common extended haplotype in white SLE patients (Kemp, M. E. et al., *Arthritis and Rheumatism* 30:1015–22 (1987)). Several C4AQ0-containing haplotypes have a DNA deletion of approximately 30 kB, extending from the 5' end of the C4A gene to the same position in the C4B gene. This deletion has been classically identified using Southern blotting, and has been found to be a genetic marker for SLE (Kemp, M. E. et al., *Arthritis and Rheumatism* 30:1015–22 (1987)). Southern blotting, however, is a time consuming and labor intensive process.

SUMMARY OF THE INVENTION

The invention pertains to methods of identifying a deletion in the C4A gene which extends from the 5' end of the C4A gene to the same position in the C4B gene, and which serves as a marker for systemic lupus erythematosus (SLE). The deletion, referred to herein as "C4AQ0," is an approximately 30 kb deletion that is associated with the extended haplotype B8,BfS:C2C,C4AQ0,C4B1;DR3, which is the most common extended haplotype in white SLE patients (Kemp, M. E. et al., *Arthritis and Rheumatism* 30:1015–22 (1987)). The methods can be used to determine whether an individual is at risk for developing systemic lupus erythematosus, as the presence of C4AQ0 correlates with a risk of developing systemic lupus erythematosus. The methods can additionally be used to determine the C4A deletion genotype of an individual (e.g., whether an individual is homozygous for C4AQ0; heterozygous for C4AQ0; or homozygous for the absence of C4AQ0).

In one embodiment of the methods, a test sample of genomic DNA is subjected to long range polymerase chain reaction amplification of target DNA that includes a retroviral insert in intron 9 of the C4A gene, using primers that are designed such that if the genomic DNA comprises a deletion in the C4A gene, PCR products are formed, and if the genomic DNA comprising a deletion in the C4A gene, no PCR products are formed. The presence or absence of PCR products is indicative of the presence or absence of a deletion in the C4A gene. In a preferred embodiment, the primers include a forward primer that corresponds to a DNA sequence in the G11 gene (e.g., TCTAGCTTCAGTACTTCCAGCCTGT (SEQ ID NO:1)), and a reverse primer corresponding to a DNA sequence in exon 10 of the C4A gene (e.g., GATGACACAAAATACCAGGATGTGA (SEQ ID NO:2)); these primers yield PCR products of approximately 5.4 kb in the presence of C4AQ0, and yield no detectable PCR products in the absence of C4AQ0(i.e., in the absence of the deletion in the C4A gene).

In a second embodiment of the invention, a test sample of genomic DNA is subjected to long range polymerase chain reaction amplification of target DNA that includes the junction between intron 9 and the retroviral insert in intron 9 of the C4A gene, using primers that are designed such that if the genomic DNA comprises a deletion in the C4A gene, no PCR products are formed, and if the genomic DNA comprising a deletion in the C4A gene, PCR products are formed. The presence or absence of PCR products is indicative of the absence or presence of the deletion in the C4A gene. In a preferred embodiment, the primers include a forward primer that corresponds to a DNA sequence in the G11 gene (e.g., TCTAGCTTCAGTACTTCCAGCCTGT (SEQ ID NO:1)), and a reverse primer corresponding to the junction between intron 9 and the retrovrial insert in intron 9 of the C4A gene (e.g., TGGTCCCCAACATGTCTGTGCATGCTG (SEQ ID NO:3)); these primers yield PCR products of approximately 5.2 kb in the absence of C4AQ0 (i.e., in the absence of the deletion in the C4A gene), and yield no detectable PCR products in the presence of C4AQ0.

Alternatively, in another embodiment of the invention, the primers for the long range polymerase chain reaction amplification are designed such that PCR products having detectably different sizes are produced in the presence and in the absence of C4AQ0; an assessment of the size of the PCR products indicates whether C4AQ0 is present or absent.

The methods of the invention are simple to perform, provide consistent results, and can be adapted for high-throughput screening of test samples. In addition, the methods facilitate genotyping of individuals, thereby affording a quick and reliable means for identification of individuals at risk for inheriting or for developing systemic lupus erythematosus.

DETAILED DESCRIPTION OF THE INVENTION

Figure 1:
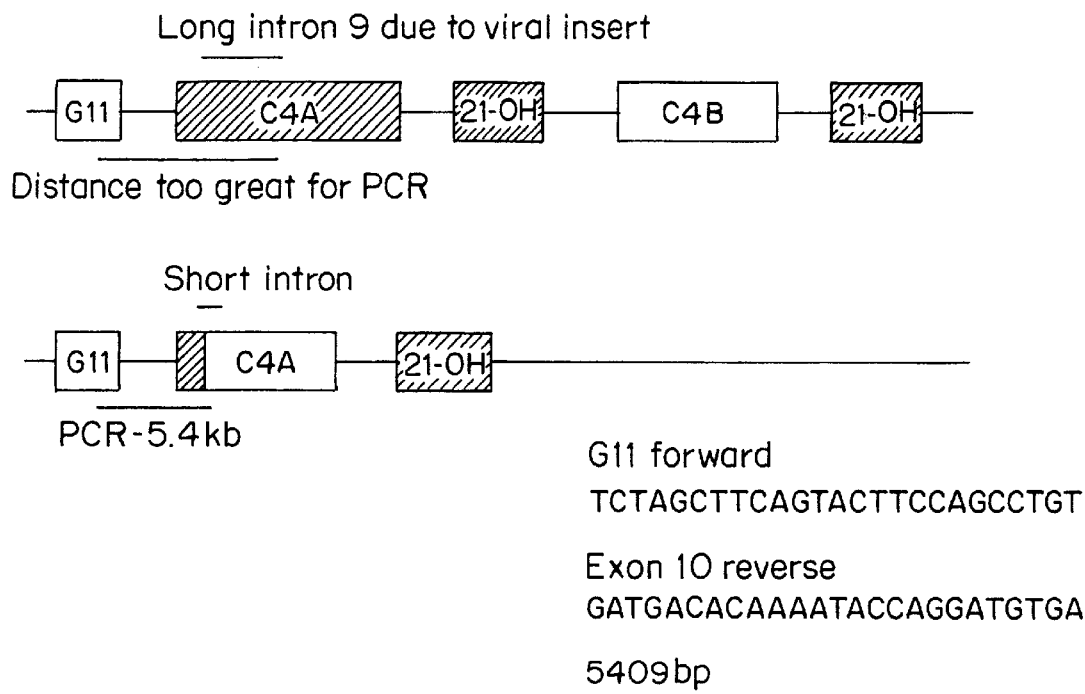
FIG. 1 is a representation of long range polymerase chain reaction (PCR) detection of the presence of C4AQ0 (presence of the deletion in the C4A gene). The G11 forward primer (SEQ ID NO:1) and the exon 10 reverse primer (SEQ ID NO:2) are shown.

The present invention relates to methods of detecting a deletion in the C4A gene, and particularly, for detecting C4AQ0, a deletion that extends from the 5' end of the C4A gene to the same position in the C4B gene. This deletion serves as a marker for systemic lupus erythematosus (SLE) (see, e.g., Kemp, M. E. et al., *Arthritis and Rheumatism* 30:1015–22 (1987); Arnett, F. C., *Clin. Immunol. Immunopathol.* 63(1):4–6 (1992)). The methods can therefore be used to identify individuals at risk for developing SLE or for inheriting SLE, or to confirm a diagnosis of SLE in an individual suspected of having SLE.

The methods take advantage of a polymorphism in the C4A gene, which results from the presence of a 6.4 kB retroviral insertion in intron 9 of the C4 gene (Chu, X., ei al., *Exp. Clin. Immunogenet.* 12:74–81(1995)). In the methods of the invention, polymerase chain reaction (PCR) amplification of long DNA sequences (herein referred to as "long range PCR" or "LR PCR") is used to amplify DNA adjacent to and including the retroviral insertion. The primers used in the LR PCR reaction are designed such that in the presence of a deletion in the C4A gene (e.g., in the presence of C4AQ0), a PCR product is produced which can be detected, and in the absence of the deletion (e.g., in the absence of C4AQ0), no PCR product is produced which can be detected, or a PCR product of a detectably different size can be detected. The absence of the deletion can be confirmed by LR PCR using primers designed such that in the absence of the deletion, a PCR product is produced which can be detected, and in the presence of the deletion, no PCR product is produced which can be detected (or PCR products of a detectably different size can be detected).

Polymerase Chain Reaction Amplification

Polymerase chain reaction (PCR) amplification is a well-known tool for amplification of nucleotide sequences. During a single cycle of PCR amplification, a double-stranded target DNA sequence is denatured; primers are annealed to each strand of the denatured target; and the primers are extended by a DNA polymerase. This cycle is repeated, generally between 25 and 40 times, in order to concentrate the number of copies of a target DNA sequence in a sample. The primers used in PCR are designed to anneal to the denatured target DNA sequence strands in a position and orientation such that the extended primers are complementary copies of the target DNA sequences. On subsequent amplification cycles, the extended primers can also serve as targets for amplification. PCR is described in detail in U.S. Pat. Nos. 4,683,202; 4,683,195; 4,800,159; and 4,965,188; the entire teachings of these patents are incorporated herein by reference. "Long range" PCR utilizes amplification conditions which improve target strand denaturation (e.g., higher denaturation temperatures, addition of cosolvents), and which protect DNA from degradation; utilizes longer extension times; and minimize incorporation of erroneous nucleotides by utilizing polymerases having exonuclease activity to reduce mismatches, thereby enabling amplification of extended strands of DNA. Long range PCR is described in detail, for example, in U.S. Pat. No. 5,512,462; in Burland, V. and Kusukawa, N., *Biotechniques* 23:1070–1072, 1074–1075 (1997)); and Cheng, S. et al., *Proc. Natl. Acad. Sci. USA* 91:5695–5699 (1994)); the entire teachings of which are incorporated by reference herein.

Test Sample

In the methods of the invention, a test sample comprising genomic DNA is used. The test sample is obtained from an individual suspected of having (or of carrying a defect associated with) systemic lupus erythematosus (SLE) (the "test individual"). The individual can be an adult, child or fetus. The test sample can be from any source which contains genomic DNA, such as a blood or tissue sample (e.g., from skin or other organs). In a preferred embodiment, the test sample is obtained from a blood sample, a fibroblast skin sample, from hair roots, or from cells obtained from the oral cavity (e.g., via mouthwash). In another preferred embodiment, the test sample is obtained from fetal cells or tissue by appropriate methods, such as by amniocentesis or chorionic villus sampling. The test sample is subjected to LR PCR amplification, and the presence or absence of a deletion in the C4A gene is then detected.

Primers

To conduct LR PCR, primers are designed to amplify DNA adjacent to, and including at least part of, DNA containing the retroviral insert in the C4A gene. The retroviral insert in the C4A gene (or part thereof) that is targeted for amplification is referred to herein as the "target" DNA. The term "primer," as used herein, refers to an oligonucleotide that is capable of serving as an initiation point for nucleic acid synthesis during PCR, under appropriate conditions as described below. The primer typically ranges from 15 to 50 nucleotides, and/or has a $T_m$ of approximately 50–75° C.; preferably, the primer is approximately 25–30 nucleotides in length, and/or has a $T_m$ of approximately 60–65° C. Primers can be prepared by a variety of methods, including chemical synthesis (see, e.g., Narang et al., *Meth. Enzymol.* 68:90–99 (1979); Brown et al., *Meth. Enzymol.* 68:109–151 (1979); Beucage et al., *Tetrahedron Lett.* 22:1859–1862 (1981); U.S. Pat. No. 4,458,066; the entire teachings of these references are incorporated herein in their entirety). The primers are designed such that the PCR products (as described below) obtained from the primers will differ in size, depending on the presence or absence of the deletion in the C4A gene (e.g., the presence or absence of C4AQ0). That is, in the presence of the deletion, the primers will yield PCR products of a certain (first) size, and in the absence of the deletion, the same primers will yield PCR products of a (second) size that is detectably different from the size of the PCR products in the presence of the deletion (the first size). A "detectably different" size indicates that the differences in the sizes of the products can be identified, using standard techniques, such as described below. In another embodiment, the primers are designed such that no PCR products are produced either in the presence or in the absence of the deletion. For example, in one embodiment, the primers will yield PCR products of a certain size in the presence of the deletion, and will yield no PCR products in the absence of the deletion. Alternatively, in another embodiment, the primers will yield PCR products of a certain size in the absence of the deletion, and will yield no PCR products in the presence of the deletion.

The nucleotide sequences of the primers correspond to DNA sequences adjacent to or present in the C4A gene or the retroviral insert (the target DNA). A primer that "corresponds to" a DNA sequence is a primer that has the same nucleotide sequence as the DNA sequence, or that is sufficiently complementary to the DNA sequence that it hybridizes under PCR conditions to the DNA sequence. A DNA sequence that is "adjacent to" the C4A gene is a DNA sequence that is in physical proximity to the C4A gene on chromosome 6, such as a DNA sequence in a gene next to the C4A gene (e.g., the G11, C2, TEN, Bf, 21-OH or RD genes, preferably the G11 gene). An "upstream" "forward" primer (a primer that hybridizes to the non-coding strand of the target DNA and forms the 5' end of the amplified product of the coding strand) and a "downstream" or "reverse" primer (a primer that hybridizes to the coding strand of the target DNA a forms the 5' end of the amplified product of the non-coding strand) are used.

To detect the presence of a deletion in the C4A gene (e.g., the presence of C4AQ0), the forward primer corresponds to a unique DNA sequence upstream of the target DNA (e.g., a forward primer corresponding to a DNA sequence in the G11 gene), and the reverse primer corresponds to a DNA sequence in an exon of the C4A gene that is after (downstream of) the location of the retroviral insert (e.g., the second half of intron 9, exon 10, or beyond). To detect the absence of a deletion in the C4A gene (e.g., to detect the absence of C4AQ0, or to detect the presence of the retroviral insert), the same forward primer as described above is used; the reverse primer corresponds to a DNA sequence within the retroviral sequence (e.g., the DNA sequence in the junction between the retroviral sequence and intron 9). In one embodiment of the invention, to detect the presence of C4AQ0, the forward primer TCTAGCTTCAGTACTTC-CAGCCTGT (SEQ ID NO:1), which corresponds to a DNA sequence in the G11 gene, is used, and the reverse primer GATGACACAAAATACCAGGATGTGA (SEQ ID NO:2), which corresponds to a DNA sequence in exon 10 of the C4A gene, is used. In another embodiment of the invention, to detect the absence of C4AQ0, the same forward primer TCTAGCTTCAGTACTTCCAGCCTGT (SEQ ID NO: 1) is used, and the reverse prime TGGTCCCCAACATGTCTGT-GCATGCTG (SEQ ID NO:3), which corresponds to a DNA sequence of the junction between the retroviral sequence and intron 9 of the C4A gene, is used.

PCR Conditions

The test sample of genomic DNA and the primers are used in LR PCR amplification. Long range PCR amplification is performed, for example, as described U.S. Pat. No. 5,512, 462. Briefly, the test sample of genomic DNA and the primers are mixed in an amplification reaction mixture. An "amplification reaction mixture" contains reagents necessary for amplification of the target DNA sequence (e.g., nucleotides, enzymes, buffers, etc.). Representative amplification reaction mixtures include commercial kits, such as the rTth DNA POLYMERASE XL kit (Perkin Elmer catalog number N808-0187). The amplification reaction mixture, including the test sample and primers, is then subjected to cycles of varying temperature. If a commercial kit is used, the manufacturer's suggested protocol can be used for amplifying the target DNA.

In one embodiment of the invention, a 20 $\mu$l reaction mixture can be used, including the following components:

| Template DNA (genomic) | 1 $\mu$l (approximately 100 ng) |
| 3.3 × Buffer | 6 $\mu$l (e.g., rTth Polymerase XL kit buffer, Perkin-Elmer) |
| MgOAc | 0.8 $\mu$l (Final: 1 mM) |
| dNTP (2 mM) | 2 $\mu$l (Final: 200 $\mu$M) |
| Forward primer (5 $\mu$M) | 2 $\mu$l (Final: 0.5 $\mu$M) |
| Reverse primer (5 $\mu$M) | 2 $\mu$l (Final: 0.5 $\mu$M) |
| rTth polymerase | 0.4 $\mu$l** |
| Water | 5.8 $\mu$l |

**rTth pol has exonuclease activity; PCR is started immediately after addition of rTth pol, which is added last to the mixture.

The reaction mixture is then subjected to cycling conditions, such as the following:
1 cycle:
94° C. for 30 sec
35 cycles:
90° C. for 10 sec
55° C. for 10 sec
65° C. for 10 min.
hold at 4° C.

Analysis of PCR Products

Following the LR PCR amplification reaction, the PCR products, if any, are detected. The term, "PCR products," refers to copies of the target DNA sequence that are produced during PCR amplification (i.e., DNA which has been amplified during the PCR process). If no DNA has been amplified during PCR, no PCR products will be generated. Analysis of the PCR products includes detecting the presence (or absence) of detectable PCR products; in a preferred embodiment, analysis of the PCR products includes determining the size of any detectable PCR products. The PCR products can be detected by a variety of methods; in a preferred embodiment, methods which separate the DNA by size, such as gel electrophoresis (e.g., agarose or acrylamide gel electrophoresis), or HPLC, are used to separate PCR products, and are followed by detection of the size fractionated DNA by methods such as staining (e.g., with ethidium bromide), or hybridization of labeled probes. Representative methods are described in *Current Protocols in Molecular Biology,* Ausubel, F. et al., eds., John Wiley & Sons, including all supplements through 1999. In a preferred embodiment, ethidium bromide agarose gel electrophoresis is used, and the presence or absence of PCR products is then detected.

Determination of the Presence of A C4A Deletion

The presence of absence of a deletion in the C4A gene can be determined based on the presence or absence, or the size, of the PCR products. For example, as shown in FIG. 1, if the test sample comprises genomic DNA containing C4AQ0, then a forward primer in the G11 gene and a reverse primer in exon 10 (e.g., SEQ ID NO:1 and SEQ ID NO:2) will yield a PCR product of approximately 5.4 kb. If the test sample comprises genomic DNA that does not contain C4AQ0, the DNA between these primers will be approximately 11.8 kb, which is too big a product to be generated (that is, no PCR products will be generated). Thus, detection of a PCR product, and particularly of a PCR product of approximately 5.4 kb, is indicative of the presence of a deletion, and particularly of the presence of C4AQ0 which is associated with SLE. Lack of a PCR product is indicative of the absence of C4AQ0.

Figure 2:
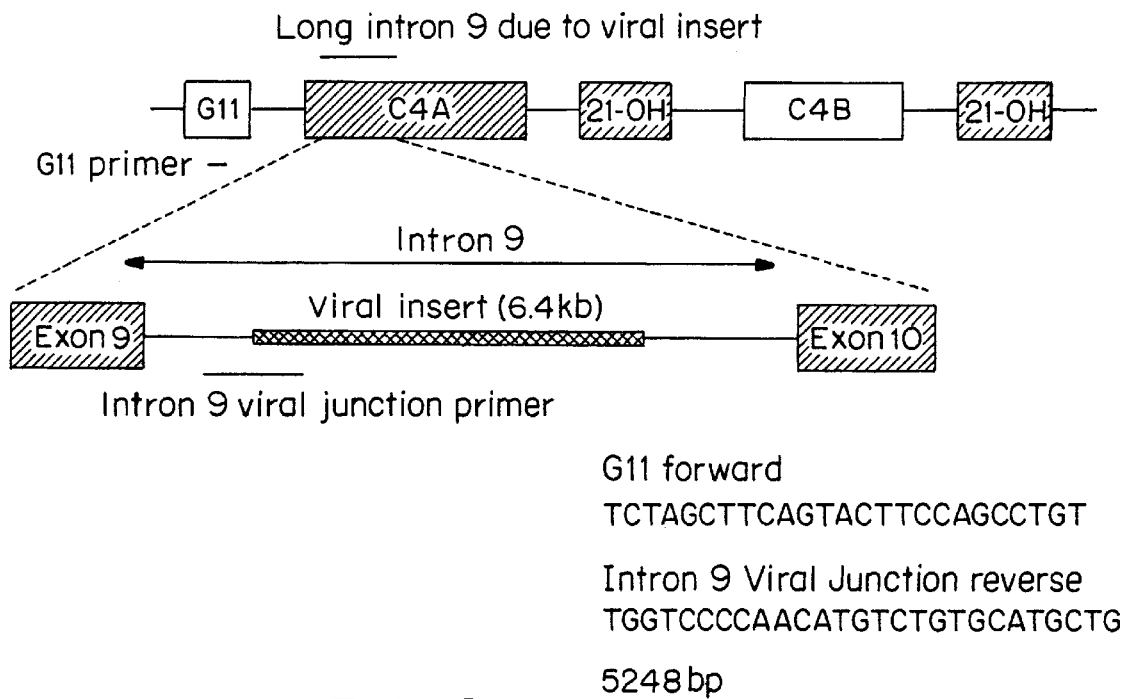
FIG. 2 is a representation of long range polymerase chain reaction (PCR) detection of the absence of C4AQ0 (absence of the deletion in the C4A gene). The G11 forward primer (SEQ ID NO:1) and the reverse primer corresponding to a DNA sequence of the junction between the retroviral sequence and intron 9 of the C4 a gene (SEQ ID NO:3) are shown.

If a PCR product is detected (i.e., if the test sample contains genomic DNA that comprises a deletion, such as C4AQ0), further experiments can also be performed to determine whether the test sample is homozygous or heterozygous for the deletion (e.g., heterozygous or homozygous for C4AQ0). For example, a forward primer in the G11 gene (e.g., SEQ ID NO:1) is used, and a reverse primer which corresponds to a DNA sequence of the junction between the retroviral sequence and intron 9 of the C4A gene (e.g., SEQ ID NO:3) is used. As shown in FIG. 2, if the test sample comprises genomic DNA that does not contain the deletion (i.e., is heterozygous for C4AQ0), these primers will yield a PCR product of approximately 5.2 kb. If the test sample comprises genomic DNA that does contain the deletion (i.e., is homozygous for C4AQ0), no PCR products will be generated. Thus, detection of a PCR product, and particularly of a PCR product of approximately 5.2 kb, is indicative of the absence of the deletion, and particularly the absence of C4AQ0. Lack of a PCR product is indicative of the presence of the deletion, particularly the presence of C4AQ0 which is associated with SLE.

Determination of Risk of an Individual for Developing SLE and C4A Deletion Genotyping Using the methods described above, a test sample of genomic DNA from an individual, such as an individual suspected of being at risk for developing or inheriting SLE, is analyzed for the presence or absence of a deletion in the C4A gene (e.g., for the presence or absence of C4AQ0). If a test sample from the individual comprises genomic DNA that contains a deletion in the C4A gene (e.g., the presence of C4AQ0), the presence of the deletion therefore indicates that the individual is at risk for developing SLE.

In addition, using the methods described above, a test sample of genomic DNA from an individual can be analyzed for the presence or absence of deletions in the C4A gene (e.g., for the presence or absence of C4AQ0), and the C4A deletion genotype (for example, whether the individual is homozygous for (the presence of) C4AQ0; heterozygous for C4AQ0; or homozygous for the absence of C4AQ0) can be determined For example, a test sample comprising genomic DNA from the individual can be subjected to long range polymerase chain reaction amplification of target DNA comprising a retroviral insert in intron 9 of the C4A gene, as described above. If the test sample comprises genomic DNA comprising a deletion in the C4A gene, PCR products are formed, and if the test sample does not comprise genomic DNA comprising a deletion in the C4A gene, no PCR products are formed; thus, the presence of PCR products indicates that the individual is either homozygous or heterozygous for a deletion in the C4A gene (e.g., C4AQ0), and the absence of PCR products indicates that the individual is homozygous for the absence of a deletion in the C4A gene (e.g., C4AQ0). Homozygosity or heterozygosity for the deletion can be determined by subjecting a test sample comprising genomic DNA from the individual to long range polymerase chain reaction amplification of target DNA comprising a junction between intron 9 and retroviral insert in intron 9 of the C4A gene, as described above. If the test sample comprises genomic DNA comprising a deletion in the C4A gene (e.g., C4AQ0), no PCR products are formed, and if the test sample does not comprise genomic DNA comprising a deletion in the C4A gene, PCR products are formed; the absence of PCR products indicates that the individual is homozygous for a deletion in the C4A gene (e.g., C4AQ0), and the presence of PCR products indicates that the individual is heterozygous for a deletion in the C4A gene (e.g., C4AQ0). This method provides an advantage over protein-based methods of analysis, as the C4A protein is produced in very low amounts, rendering it difficult to determine genotype by analysis of the amount of C4A protein.

Genotyping allows an assessment of an individual's risk for developing (or inheriting) SLE. Individuals with no deletion are at a reduced risk of developing SLE, compared with individuals with one or more deletions. At least one C4AQ0 (i.e., a heterozygous or homozygous genotype) has been identified in up to 50% or more patients with SLE, and homozygosity for C4AQ0 is reported in 11–13% of SLE patient compared to 2–3% of controls (Schur, P. H., Dubois' Lupus Erythematosus $5^{th}$ ed:254–261 (1977); Arnett, F. C., Moulds, J. M., *Clin. Exp.Rheumatol.* 9:289–296 (1991); Ratnoff, W. D., *Rheumatic. Dis. Clin. N. Am.* 22:75–94 (1996); Kumar, A. et al., *Clin. Immunol. Immunopathol.* 60:55–64 (1991); Fielder, A. H. et al., *Br. Med. J.* (*Clin. Res. Ed.*) 286 (6363):425–8 (1983); Reveille, J. D. et al., *Immunogenetics* 21(4):299–311 (1985)).

Further Embodiments of the Invention

Although the methods of the invention have been described with regard to analysis of the C4A gene for the presence of absence of a deletion (e.g., for the presence or absence of C4AQ0), the methods are also applicable to analysis of other genes for the presence of absence of deletions, duplications, insertions, and inversions (referred to collectively herein as "alterations") in a gene of interest. The methods are particularly useful for the identification of similar deletions within the genes of the major histocompatibility complex (MHC) region, as they enable analysis of sizable regions of DNA such as that of the MHC. The methods can be employed, for example, in assessment of mutations and/or deletions associated with complement-based diseases, such as rheumatoid arthritis, ankylosing spondylitis, scleroderma, and subacute sclerosing panencephalitis.

To use the present methods for analysis of a region of DNA for the presence or absence of a particular alteration in a gene of interest, primers are designed to amplify regions of DNA including and/or surrounding the alteration. Of particular importance is the annealing temperature ($T_m$) of the primers; the annealing temperature should be designed to ensure success of the polymerase chain reaction under the conditions necessary for long range PCR amplification. For example, as described above, the $T_m$ of the primers should be approximately 50–75° C., preferably approximately 60–65° C. The primers are designed such that the PCR products, as described above, that are obtained from the primers will differ in size, depending on the presence or absence of the alteration in the gene of interest. That is, in the presence of the alteration, the primers will yield PCR products of a certain (first) size, and in the absence of the alteration, the same primers will yield PCR products of a (second) size that is detectably different from the size of the PCR products in the presence of the alteration (the first size). Alternatively, the primers are designed such that no PCR products are produced either the presence or in the absence of the alteration. For example, the primers will yield PCR products of a certain size in the presence of the alteration, and will yield no PCR products in the absence of the alteration; alternatively, the primers will yield PCR products of a certain size in the absence of the alteration, and will yield no PCR products in the presence of the alteration.

A test sample is obtained as described above, and long range PCR is performed as described. The PCR products, if any, are then assessed for the presence or absence of an alteration in the gene of interest, using the methods as described above. The presence or absence of the PCR products, or the presence of PCR products of particular sizes, is indicative of the presence or absence of the alteration in the target gene of interest.

The following Examples are offered for the purpose of illustrating the present invention and are not to be construed to limit the scope of this invention. The teachings of all references cited herein are hereby incorporated herein by reference.

EXAMPLE

EXAMPLE 1
Detection of the Presence or Absence of a Deletion in the C4A Gene that is Associated with SLE Nine individuals having different genotypes were assessed (3 homozygous for C4AQ0 (the "deletion"), 3 heterozygous for the deletion, 3 homozygous for no deletion) to determine the presence or absence of C4AQ0 using long range PCR. Genotypes of the individuals had been previously determined using analysis of C4 protein. The homozygotes for C4AQ0, and the heterozygotes for C4AQ0, all had SLE. DNA from peripheral white blood cells was used in the samples. The samples were subjected to LR PCR amplification, using rTth Polymerase XL kit (Perkin-Elmer). The amplification reaction mixture included the following components:

| | |
|---|---|
| Template DNA (genomic) | 1 μl (approximately 100 ng) |
| 3.3 × Buffer | 6 μl |
| MgOAc | 0.8 μl (Final: 1 mM) |
| dNTP (2 mM) | 2 μl (Final: 200 μM) |
| Forward primer (5 μM) | 2 μl (Final: 0.5 μM) |
| Reverse primer (5 μM) | 2 μl (Final: 0.5 μM) |
| rTth polymerase | 0.4 μl |
| Water | 5.8 μl |

For the forward primer, TCTAGCTTCAGTACTTC-CAGCCTGT (SEQ ID NO:1) ("primer 1"), which corresponds to a DNA sequence in the G11 gene, was used. For the reverse primer, either GATGACACAAAATACCAG-GATGTGA (SEQ ID NO:2) ("primer 2"), which corresponds to a DNA sequence in exon 10 of the C4A gene, or TGGTCCCCAACATGTCTGTGCATGCTG (SEQ ID NO:3) ("primer 3"), which corresponds to a DNA sequence in the junction between the retroviral sequence and intron 9 of the C4A gene, was used. Because rTth pol has exonuclease activity; PCR was started immediately after addition of rTth pol, which is added last to the mixture. The reaction mixture was subjected to the following cycling conditions:

1 cycle:
94° C. for 30 sec
35 cycles:
90° C. for 10 sec
55° C. for 10 sec
65° C. for 10 min.
hold at 4° C.

The PCR products were loaded with standard loading buffer (0.25% bromophenol blue; 40% (w/v) sucrose in water) on a 0.8% ethidium bromide agarose gel, run in 1×TBE at 70V for 45 minutes, and visualized under ultraviolet light.

The results indicated that, for individuals with a homozygotic or heterozygotic deletion in the C4A gene extending from the 5' end of the C4A gene to the same position in the C4B gene (i.e., homozygotic or heterozygotic for C4AQ0), primers 1 and 2 yielded a 5.4 kB PCR product. For individuals with no deletion (i.e., homozygotic normal), no detectable PCR product was produced. For individuals with a heterozygol deletion, primers 1 and 3 yielded a 5.2 kB PCR product.

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of detecting the presence or absence of a C4AQ0 deletion in the C4A gene, comprising:
 a) subjecting a test sample comprising genomic DNA to long range polymerase chain reaction amplification of target DNA comprising a retroviral insert in intron 9 of the C4A gene, wherein the long range polymerase chain reaction amplification utilizes a forward primer that corresponds to a DNA sequence in the G11 gene, and a reverse primer that corresponds to a DNA sequence in exon 10 of the C4A gene, such that if the test sample comprises genomic DNA comprising a C4AQ0 deletion in the C4A gene, PCR products are formed, and if the test sample does not comprise genomic DNA comprising a C4AQ0 deletion in the C4A gene, no PCR products are formed; and
 b) detecting the presence or absence of the PCR products, wherein the presence of PCR products is indicative of the presence of a C4AQ0 deletion in the C4A gene in the test sample, and the absence of PCR products is indicative of the absence of a C4AQ0 deletion in the C4A gene in the test sample.

2. The method of claim 1, wherein PCR products, if present, are approximately 5.4 kb in size.

3. The method of claim 1, wherein the forward primer is TCTAGCTTCAGTACTTCCAGCCTGT (SEQ ID NO:1); and the reverse primer is GATGACACAAAATACCAG-GATGTGA (SEQ ID NO:2).

4. A method of detecting die presence or absence of a C4AQ0 deletion in the C4A gene, comprising:
 a) subjecting a test sample comprising genomic DNA to long range polymerase chain reaction amplification of target DNA comprising a junction between intron 9 and retroviral insert in intron 9 of the C4A gene, wherein the long range polymerase chain reaction amplification utilizes a forward primer that corresponds to a DNA sequence in the G11 gene, and a reverse primer that corresponds to a DNA sequence in the junction between intron 9 and the retroviral insert in intron 9 of the C4A gene, such that if the test sample comprises genomic DNA comprising a C4AQ0 deletion in the C4A gene, no PCR products are formed, and if the test sample does not comprise genomic DNA comprising a C4AQ0 deletion in the C4A gene, PCR products are formed; and
 b) detecting the presence or absence of the PCR products, wherein the presence of PCR products is indicative of the absence of a C4AQ0 deletion in the C4A gene in the test sample, and the absence of PCR products is indicative of the presence of a C4AQ0 deletion in the C4A gene in the test sample.

5. The method of claim 4, wherein the PCR products, if present, are approximately 5.2 kb in size.

6. The method of claim 4, wherein the forward primer is TCTAGCTTCAGTACTTCCAGCCTGT (SEQ ID NO:1); and the reverse primer is TGGTCCCAACATGTCTGTG-CATGCTG (SEQ ID NO:3).

7. A method of determining whether an individual is at risk for developing systemic lupus erythematosus, comprising:
 a) subjecting a test sample comprising genomic DNA from the individual to long range polymerase chain reaction amplification of target DNA comprising a retroviral insert in intron 9 of the C4A gene, wherein the long range polymerase chain reaction amplification utilizes a forward primer that corresponds to a DNA sequence in the G11 gene, and a reverse primer that corresponds to a DNA sequence in exon 10 of the C4A gene, such that if the test sample comprises genomic DNA comprising a C4AQ0 deletion in the C4A gene, PCR products are formed, and if the test sample does not comprise genomic DNA comprising a C4AQ0 deletion in the C4A gene, no PCR products are formed; and
 b) detecting the presence or absence of the PCR products, wherein the presence of PCR products is indicative of the presence of a C4AQ0 deletion in the C4A gene in the test sample which correlates with a risk for developing systemic lupus erythematosus.

8. The method of claim 7, wherein PCR products are, if present, are approximately 5.4 in size.

9. The method of claim 7, wherein the forward primer is TCTAGCTTCAGTACTTCCAGCCTGT (SEQ ID NO:1); and the reverse primer is GATGACACAAAATACCAG-GATGTGA (SEQ ID NO:2).

10. A method of determining whether an individual is at risk for developing systemic lupus erythematosus, comprising:
 a) subjecting a test sample comprising genomic DNA from the individual to long range polymerase chain reaction amplification of target DNA comprising a junction between intron 9 and retroviral insert in intron 9 of the C4A gene, wherein the long range polymerase chain reaction amplification utilizes a forward primer that corresponds to a DNA sequence in the G11 gene, and a reverse primer that corresponds to a DNA sequence in the junction between intron 9 and the retroviral insert in intron 9 of the C4A gene, such that if the test sample comprises genomic DNA comprising a C4AQ0 deletion in the C4A gene, no PCR products are formed, and if the test sample does not comprise genomic DNA comprising a C4AQ0 deletion in the C4A gene, PCR products are formed; and
 b) detecting the presence or absence of the PCR products, wherein the absence of PCR products is indicative of the presence or a C4AQ0 deletion in the C4A gene in the test sample which correlates with a risk for developing systemic lupus erythematosus.

11. The method of claim 10, wherein the PCR products, if present, are approximately 5.2 kb in size.

12. The method of claim 10, wherein the forward primer is TCTAGCTTCAGTACTTCCAGCCTGT (SEQ ID NO:1); and the reverse primer is TGGTCCCCAACATGTCTGTG-CATGCTG (SEQ ID NO:3).

13. A method of determining C4A deletion genotype of an individual, comprising:
 a) subjecting a test sample comprising genomic DNA from the individual to long range polymerase chain reaction amplification of target DNA comprising a retroviral insert in intron 9 of the C4A gene, wherein the long range polymerase chain reaction amplification utilizes a forward primer that corresponds to a DNA sequence in the G11 gene, and a reverse primer that corresponds to a DNA sequence in exon 10 of the C4A gene, such that if the test sample comprises genomic DNA comprising C4AQ0, PCR products are formed, and if the test sample does not comprise genomic DNA comprising a C4AQ0, no PCR products are formed; and b) detecting the presence or absence of the PCR products, wherein the presence of PCR products indicates that the individual is either homozygous or heterozygous for C4AQ0, and the absence of PCR products indicates that the individual is homozygous for the absence C4AQ0.

14. The method of claim 12, further comprising:

a) subjecting a test sample comprising genomic DNA from the individual to long range polymerase chain reaction amplification of target DNA comprising a junction between intron 9 and retroviral insert in intron 9 of the C4A gene, wherein the long range polymerase chain reaction amplification utilizes a forward primer that corresponds to a DNA sequence in the G11 gene, and a reverse primer that corresponds to a DNA sequence in the junction between intron 9 and the retroviral insert in intron 9 of the C4A gene, such that if the test sample comprises genomic DNA comprising a C4AQ0, no PCR products are formed, and if the test sample does not comprise genomic DNA comprising C4AQ0, PCR products are formed; and b) detecting the presence or absence of the PCR products, wherein the absence of PCR products indicates that the individual is homozygous for C4AQ0, and the presence of PCR products indicates that the individual is heterozygous for C4AQ0.

* * * * *

UNITED STATES PATENT AND TRADEMARK OFFICE
CERTIFICATE OF CORRECTION

PATENT NO. : 6,225,093 B1
DATED : May 1, 2001
INVENTOR(S) : Struan Grant and Thorarinn Blöndal It is certified that error appears in the above-identified patent and that said Letters Patent is hereby corrected as shown below:

Column 11, claim 4,
Line 36, delete the word "die" and insert -- the --.

Column 11, claim 6,
Line 63, delete the reverse primer sequence and insert
-- TGGTCCCCAACATGTCTGTGCATGCTG --.

Column 12, claim 8,
Line 29, after the word "products", delete the word "are".
Line 30, after "5.4" insert -- kb --.

Column 13, claim 14,
Line 18, delete "12" and insert -- 13 --.

Signed and Sealed this

Sixteenth Day of April, 2002

JAMES E. ROGAN
Director of the United States Patent and Trademark Office

SEQUENCE LISTING

<160> NUMBER OF SEQ ID NOS: 3

<210> SEQ ID NO 1
<211> LENGTH: 25
<212> TYPE: DNA
<213> ORGANISM: Homo sapien

<400> SEQUENCE: 1
tctagcttca gtacttccag cctgt          25

<210> SEQ ID NO 2
<211> LENGTH: 25
<212> TYPE: DNA
<213> ORGANISM: Homo sapien

<400> SEQUENCE: 2
gatgacacaa aataccagga tgtga          25

<210> SEQ ID NO 3
<211> LENGTH: 27
<212> TYPE: DNA
<213> ORGANISM: Homo sapien

-continued

<400> SEQUENCE: 3
tggtccccaa catgtctgtg catgctg                                    27